(12) United States Patent
Andersson et al.

(10) Patent No.: US 7,003,349 B1
(45) Date of Patent: Feb. 21, 2006

(54) PROGRAMMING SYSTEM FOR MEDICAL DEVICES

(75) Inventors: Jonas Andersson, Johanneshov (SE); Eric Samuelsson, Järfälla (SE); Mats Arturson, Täby (SE)

(73) Assignee: St. Jude Medical AB, (SE)

( * ) Notice: Subject to any disclaimer, the term of this patent is extended or adjusted under 35 U.S.C. 154(b) by 443 days.

(21) Appl. No.: 10/149,775

(22) PCT Filed: Nov. 22, 2000

(86) PCT No.: PCT/SE00/02309

§ 371 (c)(1),
(2), (4) Date: Nov. 6, 2002

(87) PCT Pub. No.: WO01/43821

PCT Pub. Date: Jun. 21, 2001

(30) Foreign Application Priority Data

Dec. 16, 1999 (SE) .................................... 9904626

(51) Int. Cl.
*A61N 1/37* (2006.01)
(52) U.S. Cl. ................... 607/27; 600/510; 600/523
(58) Field of Classification Search ............ 607/27–32; 600/510, 523–525
See application file for complete search history.

(56) References Cited

U.S. PATENT DOCUMENTS

| 5,576,952 | A | * | 11/1996 | Stutman et al. ............. 600/300 |
| 5,713,937 | A | | 2/1998 | Nappholz et al. |
| 5,800,473 | A | | 9/1998 | Faisander |
| 5,833,623 | A | | 11/1998 | Mann et al. |
| 6,327,501 | B1 | * | 12/2001 | Levine et al. ................. 607/27 |

* cited by examiner

*Primary Examiner*—Scott M. Getzow
(74) *Attorney, Agent, or Firm*—Schiff Hardin LLP

(57) ABSTRACT

A programmer for an implantable medical device includes a display which displays a graphical representation of an area of interaction of the medical device within a patient. The graphical representation includes at least one independently selectable graphical object. The programmer includes a unit for associating parameters or functions used in controlling the medical device with the object, so that when an operator, via the programmer, selects an object, the associated parameters or functions are displayed for consultation, modification or execution. By directly linking the programmable parameter or function with an image of the device and the surrounding parts of the patient's body, the clinician is immediately presented with a clear and understandable link between the parameters and a physical entity.

28 Claims, 6 Drawing Sheets

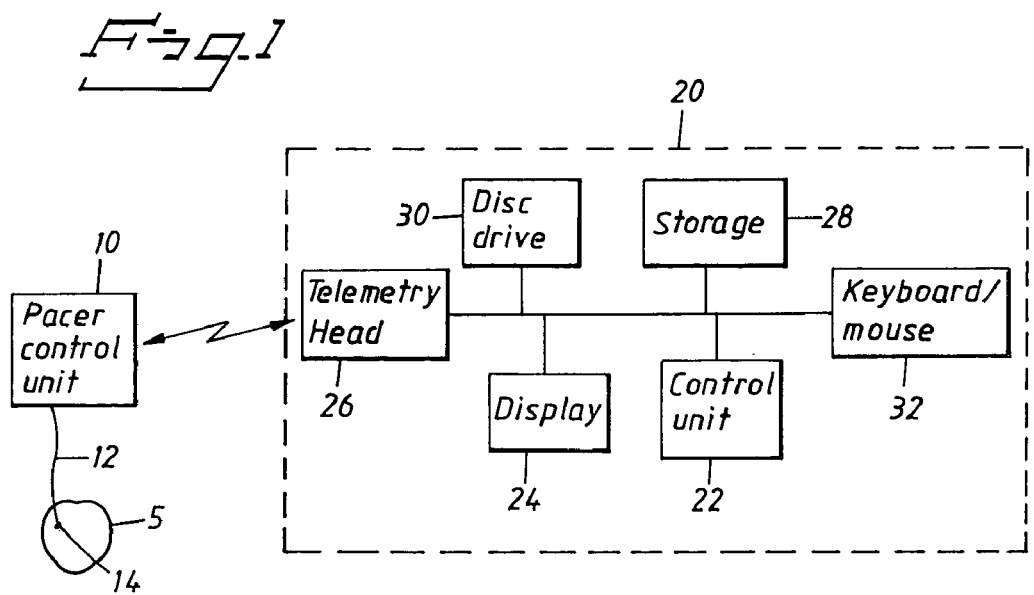
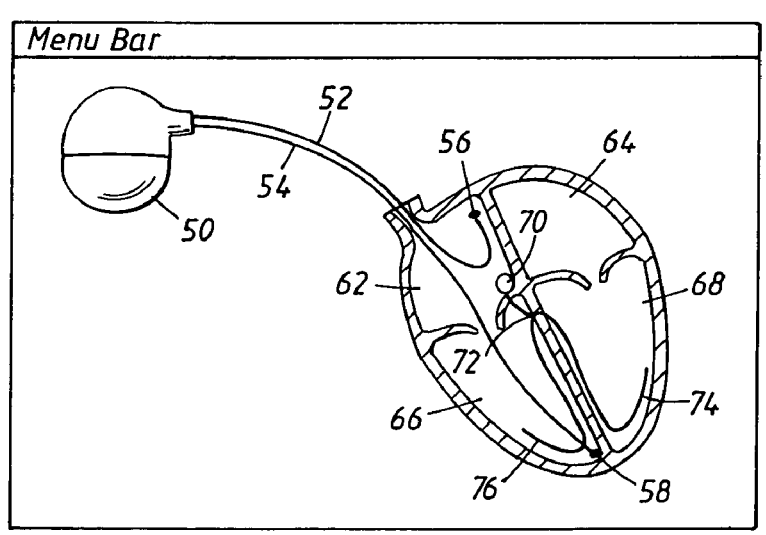

| Atrium | | | | |
|---|---|---|---|---|
| Parameters | | | | |
| Pulse amplitude | 3.5 | ▼ V | Test |
| Pulse width | 0.4 | ▼ ms | |
| Pulse current | 1 | mA | |
| Pulse energy | 2 | μA | |
| Pulse charge | 3 | μC | |
| Refractory period | 3.5 | ▼ ms | |
| Sensitivity | 0.4 | ▼ mV | Test |

[ Program ] [ Close ]

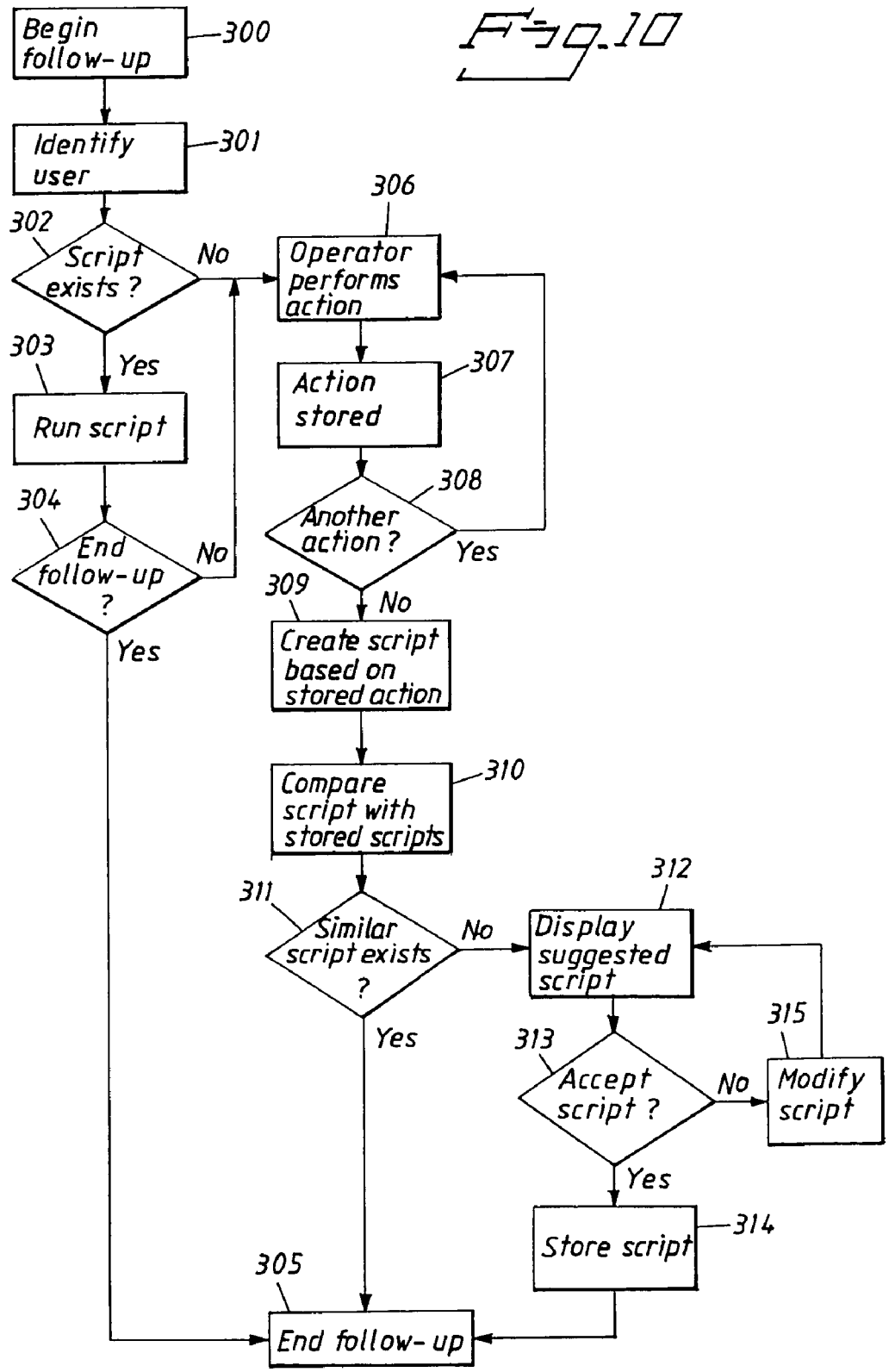

PROGRAMMING SYSTEM FOR MEDICAL DEVICES

BACKGROUND OF THE INVENTION

1. Field of the Invention

The invention relates generally to implantable medical devices and more particularly to systems for programming implantable medical devices.

2. Description of the Prior Art

Implantable medical devices perform multiple highly complex functions which may be adapted to the particular conditions and needs of specific patients. For example implantable cardiac pacers, which provide stimulating impulses to a heart with a disturbed cardiac rhythm, can be configured with various different parameters values and functions depending on the particular condition of a patient. As an example, a cardiac pacer that is presently on the market allows in excess of 40 different parameters to be programmed.

In addition to the programmable parameters, a cardiac pacer generally stores a large quantity of measured data. Conventional pacers are commonly equipped with sensors for monitoring the activity of the heart. Information obtained through monitoring can be used for diagnosing certain patient conditions, which in turn can be addressed by adapting the pacer functions in some way. The programming and interrogation of implanted devices is commonly performed non-invasively using a computer- or microprocessor-based programmer, which communicates with the pacer via a telemetry link. These programmers include a display and some form of keyboard, which may be implemented as a touch sensitive screen, for the input of data. When the programmer interrogates the implanted device, stored and measured data will be transferred to the programmer.

This information must be displayed to the operator. Parameter values, whether programmable, measured or fixed, are displayed as numerical or alphanumerical values. An example of such a programmer is described in U.S. Pat. No. 5,833,623. The manner in which this information is organized for display varies from programmer to programmer. U.S. Pat. No. 5,713,937 describes a display portion used to display the medical implant and its connection to the heart of a patient. A number of alphanumerical labels containing different characters indicate particular types of parameters or functions. When a user selects one of these labels, the parameters associated therewith are displayed and can be modified. However, conventional programmers typically display programmable parameters and measured data separately. Moreover, with the large amount of data provided by present day pacers, the programmable information in many cases is further divided into subgroups for display. For example, programmable parameters may include basic parameters, extended parameters, sensor parameters and patient data. Such groupings typically are chosen for technical reasons related to the internal organization of the programmer. For example some parameters may require additional interrogation of the pacer, while others may be more readily available. Consequently, an operator of a programmer must be very familiar with the programmer organization if he or she is to operate the programmer effectively and to full effect.

The majority of such medical devices are programmed and monitored by medically skilled practitioners, who have a thorough understanding of the patient's condition, but may have less knowledge of the possibilities of the programmer and/or the medical device. Moreover, they may be required to monitor several different types of medical devices, working in different modes and implanted in patients with different diagnoses. As a result, an operator may encounter two medical devices of the same type and configured in the same way for the same patient diagnosis only infrequently. Consequently, there is a need for a programmer that is simple to operate and which can be used intuitively.

SUMMARY OF THE INVENTION

It is thus an object of the invention to provide a programmer for monitoring and controlling the operation of an implantable device that is easy to operate, and thus enables an operator to exploit all possible functions of a medical device with little knowledge of the programmer.

The above object is achieved in accordance with the principles of the present invention in an arrangement and method for monitoring and controlling the operation of an implantable medical device, as well as a computer software product for the same purpose, wherein movable representations of a number of objects are displayed, the movable objects being combinable to form a graphical representation of an area of interaction of the medical device within the patient, and the graphical representation including at least one independently selectable object, and wherein parameters or functions for use in controlling the device are associated with the objects, and wherein selection of the objects is undertaken and, responsive to the selection, the parameters are functions associated with the selected object are displayed to enable consultation, modification or execution of the parameters or functions. The parameters or functions are then communicated to the medical device for implementation by the medical device.

By directly linking a programmable parameter with a graphical representation of the area interaction of the medical device with a patient, the physician or nurse programming the implantable device is immediately presented with a clear and understandable link between parameters and a physical object, be it part of the medical device itself or, for example, the tissues of the patient surrounding the device. In this way the workings and organization of data within a programmer is effectively hidden from the operator. The operation of resulting system is thus more intuitive for medically qualified personnel and therefore easier. In addition, patient safety and comfort are improved, since there is less likelihood of the operator selecting unsuitable parameters. Moreover, the programmer can provide the operator with all the different possible functions associated with each selected part to enable the operator to more fully exploit the functionality of the medical device.

This ease of use is still further facilitated when the operator can compose the graphical representation from a number of objects in accordance with a preferred embodiment of the invention. In this way an operator is able to tailor both the display and the programming capabilities of the programmer to his own preferences, to a patients specific needs or to the requirements of a type of implantable device. When such a custom representation is linked to a specific operator identification code or to a particular device type code, the programmer can be made to automatically display the required configuration upon identification of an operator and/or a device type, so that different operators working on different devices will automatically be presented with a display that is optimally adapted to the operators preferred manner of working or to the particular requirements of a specific device type.

Preferably an operator identification code and device type code also serve to restrict access to select parameters or functions used in controlling the implanted medical device. In this way the type of operations available to an operator can be restricted depending on the operators competence and qualifications. Hence some operators may be authorized to consult the parameter settings only; others may additionally be authorized to perform tests or other functions, while a last group of operators may be authorized to perform all available operations with the programmer. The same restrictions can be imposed on device types.

The intuitive use of the programmer is still further improved when the programmer includes means for displaying graphically a representation of at least one measurable physiological activity influenced by the medical device, wherein parameters or functions for use in controlling the device are associated with select dimensions of this representation, means for selecting and altering the shape of the displayed physiological activity to illustrate a desired operational effect of the medical device on the physiological activity, and means responsive to the altered shape for modifying the associated control parameter or executing the associated function in accordance with the modified representation.

Linking parameters to a graphical representation of a physiological activity in this way enables the operator to visually select parameter values on the basis of the effect intended. The resulting system thus is not only easier to use for a medical practitioner, it will also be safer for the patient, since there is less likelihood of the operator programming unsuitable parameter values.

To further facilitate the operation of the programmer, means are provided to record all actions of an operator, whether this concerns the selection of objects on the display, the execution of a tests function or the modification of a parameter value. These recorded actions are then compiled in a program sequence with may serve as an automatic procedure for future patient follow-ups. When the actions are recorded as a function of time, i.e. when they include information relating to the time and date of execution, the recorded information can be used as a valuable source of statistical information. An external access is preferably provided to enable the collection of this recorded data.

The invention further relates to a method for monitoring and controlling the operation of an implantable medical device and also to a computer program product.

DESCRIPTION OF THE DRAWINGS

FIG. 1 schematically shows a system for programming a medical device in accordance with the present invention.

FIG. 2 illustrates a first window of a graphical user interface of the inventive programmer, showing a graphical representation of the heart and a pacer.

FIG. 10 is a flow chart for automatically generating follow-up procedures in accordance with the invention.

DESCRIPTION OF THE PREFERRED EMBODIMENTS

Figures 3, 4:
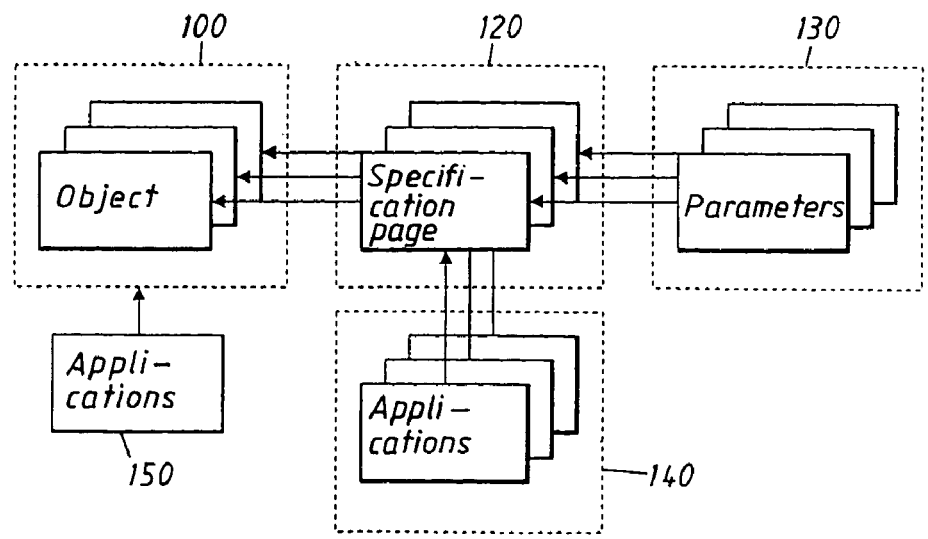
FIG. 3 illustrates a second window of the graphical user interface of FIG. 2.
FIG. 4 schematically depicts the software organization of the graphical user interface in accordance with the invention.

FIG. 1 schematically shows an arrangement for programming an implanted medical device. In the illustrated embodiment, the medical device is a cardiac pacer implanted in a patient. The pacer contains a pacer control unit 10, which is generally implanted near the shoulder of the patient under the skin and one or more electrodes 14, which are anchored in the patient's heart 5. One or more leads 12 connect the electrodes 14 to the pacer control unit 10. The pacer is capable of operating autonomously and is powered by a battery (not shown). The electrodes 14 are used to apply stimulating pulses to the heart tissue and may also sense the electrical activity of the heart and possibly other physiological activities, such as respiration. This information is stored in the pacer control unit 10, for example in the form of an intracardial electrogram (IEGM) for later consultation by a medical practitioner during a routine check. Other information collected and stored in the pacer control unit 10 can include data relating to the condition of the pacer, such as the residual battery power or the impedance of the leads 12. The information stored in a pacer can be consulted using a programmer 20 which is preferably computer-or microprocessor based.

The programmer 20 includes a control unit 22, a display 24, a telemetry head 26, internal storage unit 28 and some form of data input device 32 that may be a keyboard, a mouse, a touch-sensitive screen, or the like, or some combination of these. A disk drive 30 may also be provided in the programmer 20 for receiving a diskette, CD ROM or similar portable storage element capable of carrying computer-readable code. Software used for controlling the operation of the programmer is stored in the storage unit 28 and executed by the control unit 22 using the storage unit 28. Additional software applications can be provided on a removable diskette and read with the aid of the disk drive 30. These additional software applications may be used to optionally extend the functions of the programmer. Alternatively, additional software applications may assure more basic functions that are specific to a class of implantable device; this may be of interest when the internal storage means 28 of the programmer 20 are of limited capacity, for example. Communication between the programmer 20 and the pacer control unit 10 is effected via a telemetry link, whereby the telemetry head 26, which preferably includes an inductive coil, is placed over the implantation site of the pacer control unit 10. Once a link has been established, the programmer 20 interrogates the pacer control unit 10 and downloads the stored information. Modifications to the pacer settings programmed by the programmer 20 are also uploaded to the pacer control unit via the telemetry link. Exchanges of information between the pacer control unit 10 and the programmer 20 may occur throughout a programming session, for example to obtain recent ECG or IEGM signals recorded by the pacer 10 when testing a modified parameter value.

Interaction between the operator and the programmer 20 is through the display 24 and input device 32 and more particularly through a graphical user interface of the programmer 20.

FIG. 2 shows a first screen of the graphical user interface that is presented on the display 24 during a programming session. This screen shows a graphical representation of a cardiac pacer 50 and a patient's heart 60. The pacer representation 50 has two leads 52, 54, each connected to an electrode, 56, 58, which is shown positioned in the heart. Also shown on the display are the four separate chambers 62, 64, 66, 68 of the heart as well as the AV node 70, the bundle of His 72 and the left and right bundles 74, 76. For clarity, the illustrated window shows a highly simplified and stylized representation of the heart. It will be appreciated, however, that a more accurate representation of both the heart and the pacer components is possible and indeed preferable to enable the easy and rapid identification of the image portions by an operator.

Select components of this graphical representation are defined as separate objects and can be selected individually by the operator using the input device 30. For example, the pacer casing 50, the leads 52, 54, and the right ventricle and atrium 66, 62 are preferably each defined as a separate object. Each object is linked to a specification, such that the selection of an individual object by the operator will cause a second screen to appear on the display 24 showing the object specification. Selection may be achieved by placing a cursor over the desired object and pressing a specific key or clicking a mouse button. The object specification includes a list of all programmable and measured parameters connected with the object. If diagnostic data is available for a parameter, or a test applicable to the parameter, this is also linked to the object specification. In order that the graphical user interface may be used intuitively, the parameter values and/or functions linked to any given object shown on the first screen preferably have some logical association with that object. For example, the lower portion of the pacer 50 may be defined as an object, which when selected causes information regarding the battery to be displayed. Similarly, the objects illustrated as leads 52, 54 may each be linked to lead impedance parameters.

Preferably a selected object will be highlighted in some way, for example by a change in color or variation in the degree of luminosity on the screen to confirm the operator's selection. Alternatively, if a cursor is used, each object may be highlighted automatically as the cursor passes over the object to prevent an object from being selected erroneously.

An illustrative example will now be described with reference to FIGS. 2 and 3. Supposing that the operator selects the right atrium 62 shown in the first screen of FIG. 2, for example by placing a cursor over the right atrium and clicking with the mouse or keyboard, a second screen will then appear as shown in FIG. 3. This second screen shows the parameter values associated with the right atrium. These are the atrial pulse current, energy and charge, as well as the pulse amplitude, pulse width, refractory period and sensitivity. These latter four parameters can be modified by the operator. The object specification screen indicates this possibility, for example by providing the present parameter value against a highlighted background and providing a list of alternative values which may be selected in place of the presently programmed value. A test button is provided alongside parameters for which a test routine is available. If the operator wishes to test the effect of changing any parameter, the test application will be called up on depressing the test button. If diagnostic data were available, this would also be indicated in the object specification page.

Any modified value or values will be programmed in the pacer 10 only when the operator presses a "Program" button provided at the base of the screen. When a parameter value is changed using the object specification screen, the new value will preferably be shown in a contrasting color so that the operator can immediately recognize which values have been altered. This color will return to normal once it has been programmed. In order to help the operator keep track of the various modifications made, a programming log may be provided at the base of the first screen for listing the modified parameter values. This preferably takes the form of a narrow window through which the operator may scroll. Each time a modification is made, a brief message indicating the parameter type and the change in value is added to the list.

Preferably the object specification screen indicated in FIG. 3 does not replace the first graphical user interface screen of FIG. 2, but is rather opened as a window over the first screen. In this way, several object specification screens can be called up and displayed in parallel when one object is selected. For instance, in the example just illustrated, the specification of the atrial lead might also be displayed when the right atrium 62 is selected.

If the number of parameters linked to any single object is too great to display on a single object specification screen, a button indicating further parameters may be provided which opens a second screen when pressed.

An overview of the software organisation for the graphical user interface of the programmer 20 is schematically illustrated in FIG. 4. This includes a first module 100 defining the information displayed in the first screen of the graphical user interface. This module 100 contains the definitions of the various objects of a graphical representation, which shows the area of intervention or interaction of the medical device with a patient. Each object in the first module 100 is linked to one or more specification pages contained in a specification module 120. Each object specification page contains information regarding the various classes of parameters that are linked or mapped to the associated object. Each object specification page is in turn associated with parameter values corresponding to the mapped parameter classes. These parameter values are shown grouped in a further module 130. Applications are also linked to each specification page for providing the required test and diagnostic routines or other sub-programs that may be linked to an object via an object specification page. These applications are likewise shown grouped in a module 140 for the purposes of the overview. In addition to applications accessible solely via an object specification page, other applications may be linked directly to the first page of the graphical user interface as shown by the module 150. These applications may be accessible via a menu bar incorporated in the first screen and may include all the applications relating to test routines as well as other applications of use to the operator, such as for the generation or performance of patient follow-ups.

Figure 5:
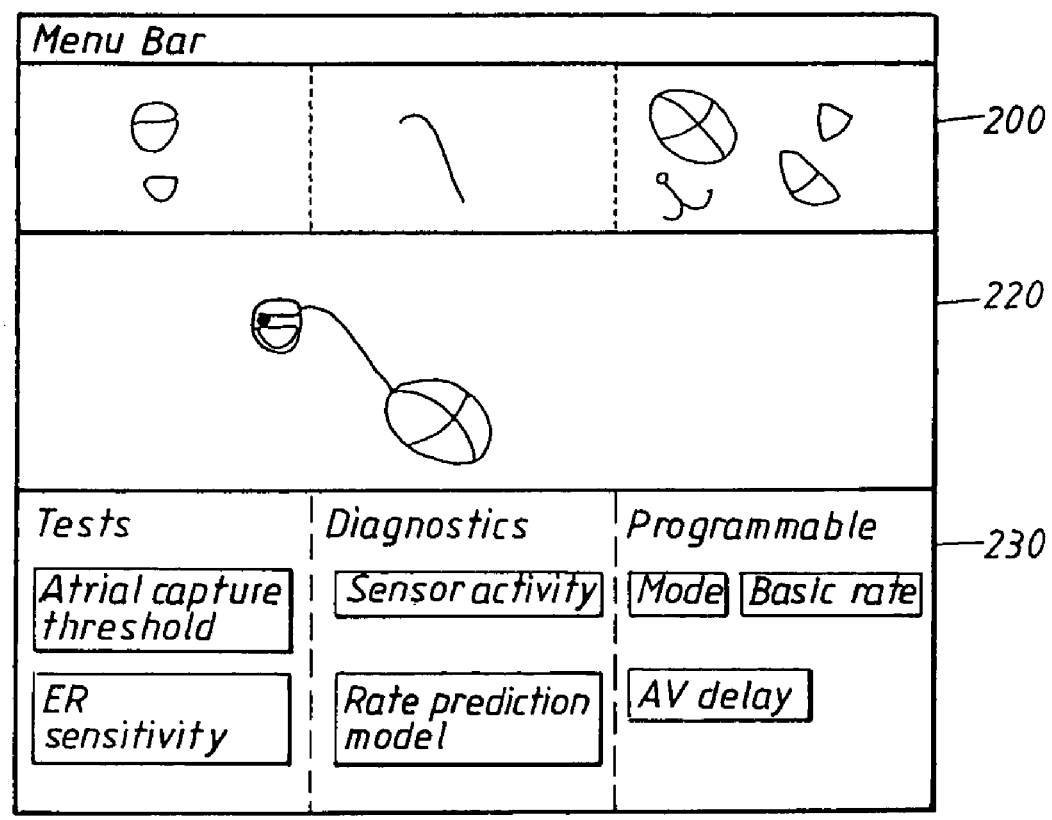
FIG. 5 illustrates an alternative embodiment for graphical representation with a divided screen, in accordance with the invention.

Turning now to FIG. 5 there will be described an embodiment of the invention which results in a more flexible graphical user interface, which may be modified according to the needs and habits of an operator, to the class of device, or to a patient's particular condition. FIG. 5 depicts a first screen according to an alternative embodiment of the graphical user interface. In this embodiment, the screen is divided into three portions. A first portion of the screen 200 contains parts of a graphical representation. More specifically, this first portion 200 is likewise subdivided into three parts and contains in one part, at the far left of FIG. 5, three elements representing parts of a pacer device, such as the casing and the battery, in a second part illustrated in the center of the portion 200 a pacer lead and in the final part on the right of FIG. 5, elements representing the heart or parts of the heart. The elements displayed in the first portion 200 of the screen are movable. This means that the operator may select various elements and combine these to form a desired graphical representation for the working model of the first screen of the graphical user interface. The second portion 220 of the screen is provided for composing the graphical representation, which will be used for programming and monitoring the implanted medical device. Specifically, the operator is required to select the desired elements one-by-one and transfer or copy these to the second screen portion 220 into a desired configuration. In FIG. 5, it is assumed that this operation already has been carried out, and the final graphical representation is presented in the second screen portion. Preferably the selection and moving of each element is accomplished by a drag-and-drop operation. When an object is selected it may be removed from the first screen portion 200. Alternatively, the elements may remain displayed in the first screen portion 200 as shown in FIG. 5 after selection and moving to the second screen portion 220.

Each element moved to the second screen portion 220 preferably represents an object that may be selected individually in the graphical user interface. After composition of the graphical representation defining the area of intervention of the medical device, specification functions are associated with each element. These functions are displayed in a third portion 230 of the screen. This portion is likewise subdivided into three and contains three classes of specification functions. The function classes are tests, diagnostics and programmable parameters. In the illustrated example, the tests include two routines, namely an atrial capture test, for determining the lowest safe atrial pulse energy, and an evoked response (ER) sensitivity test, for determining the pulse energy required to evoke a response in the ventricle of the heart. In the area of diagnostics, the operator is presented with two options, namely the examination of the activity sensed by the pacer sensors and a rate prediction model. Finally in the last part of the screen 220 containing the programmable parameters, the operator is presented with the option of permitting the programming of the basic rate, the mode and the AV delay. As for the assembly of the graphical representation, the assignment of these functions to any specific object is preferably accomplished using a drag-and-drop operation. Some functions may be assigned to more than one object. Furthermore, some parameters or applications may already be mapped to the objects, so that the operator is permitted only to add additional parameters functions. This ensures that the basic or essential information on the cardiac pacer is available to the operator. With reference to the software organization shown in FIG. 4, each additional parameter or function that can be linked to an object may be contained in its own specification page 120. Thus when an object 100 is selected all specification pages 120 or windows will be displayed, possibly superimposed on one another when required by space. Alternatively, related parameters and functions mapped to an object may be grouped in the same specification page 120.

As mentioned above, the ability to compose different graphical representations, which then serve to provide access to the multiple functions of the programmer, allows an operator to adapt the programmer to his own preferences and thus to utilize the programmer more effectively. However, this option may also be used to customize the programmer 20 for a specific type of pacer device 10, for specific patient diagnoses, or even for individual patients, thus adapting the programmer to both the type of device and the condition of the patient. This is preferably achieved by linking a customized object-oriented graphical representation with a user identification code or ID, and possibly with a pacer device ID and patient ID.

This is implemented as follows. Any user authorized to use the programmer 20 will be assigned a unique user ID, which will be stored in the storage means 24 of the programmer. The same is true for pacer devices 10 that may be programmed by the programmer 20 and may also be provided for individual, or groups of, patients. When an operator commences working with the programmer, the programmer will request the operator's personal ID. Preferably the programmer will also request a secret password which is encrypted, preferably with a one-way function, and compared with an encrypted version of the password, which is likewise stored in the storage means 24 of the programmer. The ID and password together constitute a unique operator identification code. If the password is correct and the operator correctly identified, the programmer will launch the customized object-oriented graphical user interface. In the same way, a customized graphical representation may be stored for a particular class of pacer device, or even for a particular patient diagnosis.

A user ID is preferably also utilized in combination with a password to restrict access to certain functions of the programmer on an operator-by-operator basis. In this way select functions of the programmer can be restricted to authorized users only. For example, some operators may be restricted to the viewing of diagnostic data, some may be authorized to alter restricted programmed parameter values, while other operators may have access to all available programmer functions. Similarly, if an operator id is combined with a device id or patient id, the programmer can be configured to propose only those functions that are useful for the implanted device or the condition of the patient, thus rendering the utilization of the programmer more rapid and easier for the operator. It will be understood that the restriction of access to certain programmer functions may be provided either with or without a customized object-oriented graphical user interface.

In accordance with a further embodiment of the present invention, parameter values are not programmed by typing in or selecting a numerical value but are instead also displayed in graphical form. More specifically, the programmer 20 displays a representation of a quantity that is influenced by the operation of the implanted medical device. Preferably this quantity is also measured by the implanted medical device. Preferably the quantity represents a physiological activity influenced by the device and commonly used for by a clinician for evaluating the patient's condition and also the operation of the implanted device 10. The parameters used for controlling the operation of the medical device are mapped to this representation in such a way that a variation in the shape of the representation causes the programmer to effect a corresponding variation in the value of the mapped parameters. The representation of a physiological activity is preferably in the form of a waveform. In the present example which relates to a cardiac pacer 10, the waveform is an ECG or IEGM, which is routinely measured during programmer sessions. Data representing the measured electrical activity of the heart in the form of an ECG or IEGM is also readily available from the pacer device itself. By displaying parameters in such a graphical form, and moreover, permitting the modification of parameters by manipulating the graphical representation, the operator knows immediately what effect the programmed parameters will have on the patient's condition. This is described in more detail with reference to FIG. 6.

Figure 6:
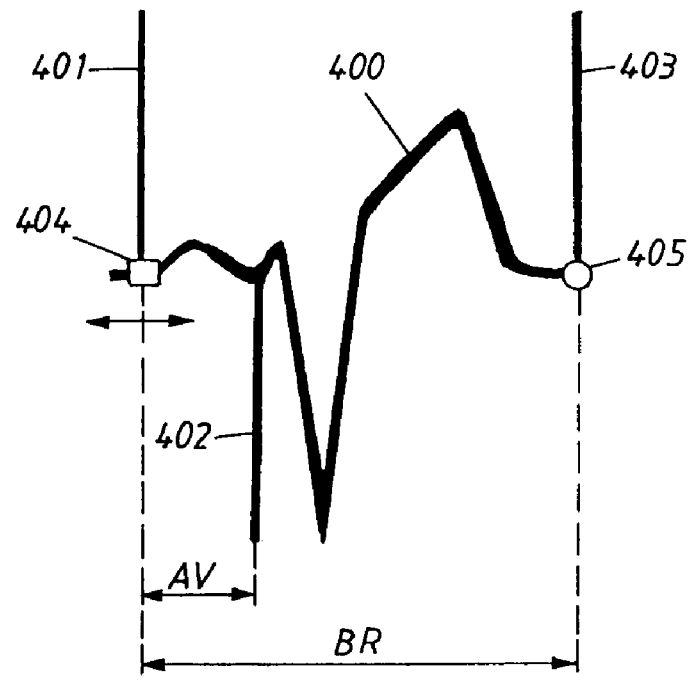
FIG. 6 shows a window of the graphical user interface for programming AV delay and the basic rate in accordance with the invention.

FIG. 6 shows a parameter programming window of the graphical user interface. It is assumed that this window is displayed by the programmer following the selection by the operator of the programmable parameter in a graphical user interface of the programmer 20. The parameter selected is the base rate of the pacer 10.

The waveform 400 depicted in this window represents one cycle of an ECG in which atrial stimulation pulse 401 and ventricular stimulation pulses 402 are shown. The atrial stimulation pulse 403 for the following cycle is also shown in the waveform. For this waveform, the programmable parameter for the basic interval BR of the pacer is mapped to the distance between the two atrial stimulation pulses 401, 403. The basic interval is the period between two consecutive paced events without intervening intrinsic activity. While the basic interval is not a common programmable parameter for most pacer devices, it is inversely proportional to the base rate, which is commonly used. The programmer may associate either base rate values or basic interval values with this distance. A further parameter, namely the AV delay, AV, also is mapped to a portion of the waveform, specifically to the distance between the first atrial stimulation pulse 401 and the ventricular stimulation pulse 402. Select points on the curve are defined as movable or fixed. In FIG. 6, the starting point 404 represented by a square is a movable point, while the end point 405 represented by a circle is a fixed point. By selecting and dragging the movable point 404, either using a cursor control device, such as a mouse, or by keyboard or keypad controls, the operator can alter the length of the curve 400, and specifically the mapped portions of the curve. Since both the basic interval BR and the AV delay AV depend on distances measured in parallel to the horizontal axis of the curve 400, the movable point 404 is constrained to move along a straight line defined by the axis (the time axis) of the curve 400.

The programmer 20, and specifically the control unit 22 automatically adjusts the parameter values linked to the dimensions of the curve 400. For example if the operator moves the movable point to the left in FIG. 6 to lengthen the curve, the basic interval will be lengthened and the base rate reduced accordingly. Similarly, a reduction in the curve length by moving the movable point to the right in the figure will reduce the basic interval. Once an operator has made the desired adjustment to the curve, he or she may program the pacer device 10 with the associated parameter values. This is preferably achieved by providing a separate "program" command button on the screen. On registering this command, the control unit 22 of the programmer 20 sends the new parameter values to the pacer device 10 through the telemetry head 26. Only basic interval or base rate values allowed by the pacer device will be programmed. Thus if the pacer permits specific discrete values of base rate only, the programmer will set the permitted value that is closest to that defined by the modified curve. In the same way, the upper and lower limits of any parameter value is similarly observed. The upper and lower limits of a parameter are preferably also illustrated graphically by preventing further movement of the curve when a limit has been reached. In addition the two end points of any parameter value may be illustrated graphically as limits to the curve variation to aid the operator in scaling any adjustment.

When the movable point 404 of the curve is shifted, this causes a stretching of the curve throughout its length. Thus all the intervals defined along its length will be modified in scale with the increase in length. In other words, the curve 400 retains its relative proportions in the direction of movement in analogy with normal physiological processes. Thus in the curve depicted in FIG. 6, an increase in the basic interval BR caused by the extension of the curve width will automatically cause an in-scale variation of the AV delay. When the operator programs a modified base rate, the control unit 22 will automatically send the adjusted AV delay value to the pacer 10. Other parameters that are likewise affected by a variation in the basic interval, such as the PV delay or the refractory period, also could be associated with the curve. This permits different parameters to be altered and programmed using the same curve. For example supposing that at a base rate of 90 pulses per minute (ppm), the AV interval, AV, must not exceed 300 ms. The restriction in the value of AV delay, AV, may be automatically implemented by the programmer when the operator adjusts the base rate by altering the total length of the curve 400.

Different parameters may also be programmed independently using the same curve. For the programming of each separate parameter, a different set of fixed 405 and movable points 404 are displayed. The different programmable parameters may be selected by the operator using an appropriate command from a menu bar incorporated in the parameter programming window. Alternatively, or in addition, the desired parameter may be selected by selecting the appropriate portion of the curve 400 to make movable 404 and fixed points 405 appear.

Figure 7:
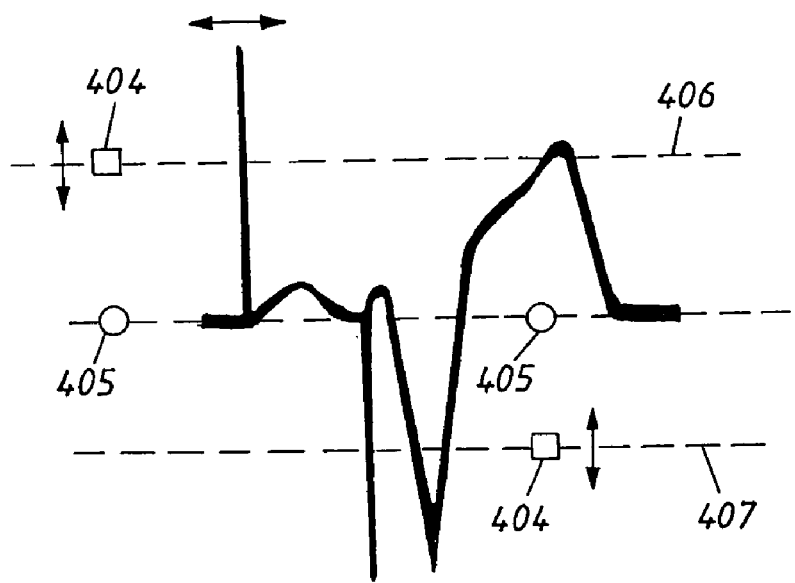
FIG. 7. shows a window of the graphical user interface for programming capture threshold and evoked response sensitivity in accordance with the invention.
Figure 8:
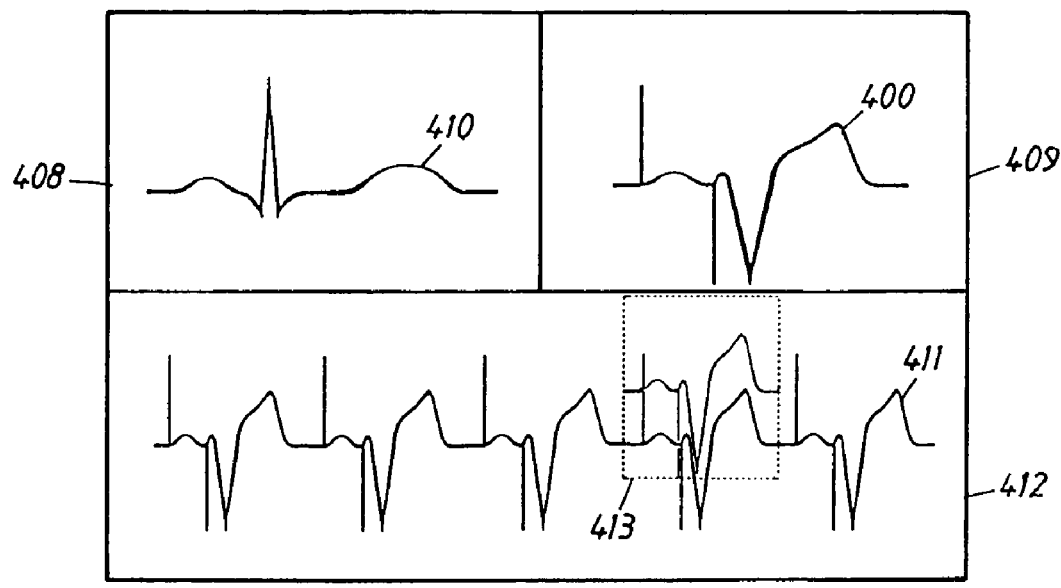
FIG. 8 shows a screen of the graphical user interface for programming parameter values according to a further embodiment of the invention.

The representation of parameters in terms of their effect on a physiological activity as illustrated in FIG. 6 preferably also utilized for the depiction of diagnostic tests and measured data. This is shown by way of example in FIG. 7 which shows the invention using a parameter programming screen as depicted in FIG. 8. The screen in FIG. 8 is divided into an upper and a lower portion, with two windows 408, 409 in the upper portion and a single window 412 comprised in the lower portion. The two upper windows 408, 409 show waveforms used for programming parameters. The waveform 400 representing an ECG cycle showing atrial and ventricular stimulation is depicted in the right upper window 409 and a waveform 410 representing a spontaneous ECG cycle 410 is depicted in the left upper window 408. As mentioned above, these two waveforms 400, 410 can be used to program substantially all programmable parameters of a cardiac pacer, as well as illustrating tests and diagnostics. In the third window 412 depicted in the lower half of the screen there is displayed a continuously rolling waveform 411 constructed from data recorded by the pacer device or the programmer. The operator changes the shape of the waveforms 400, 410 in the two uppermost windows 408, 409 to program parameters and can observe the result on the recorded waveform 411 depicted in the lower window 412. In order to compare the results between the desired programmed values input via the waveforms 400 or 410 and the resulting measured waveform 411, the programming waveforms 400 and 410 may be copied and superimposed on parts of the measured waveform 411. This is illustrated in the lower window 412 of FIG. 8. Preferably this is implemented using a drag and drop function so that the operator may simply select the programming waveform 400, 410 and drag down the resulting copy 413 to the measured waveform 412 for comparison. The displaced waveform is automatically modified to the scale of the measured waveform 411 to enable a useful comparison. A freeze function is associated with the recorded waveform 411 and may be invoked to facilitate this comparison.

The waveforms 400 and 410 may be stylized waveforms stored in the programmer before use. Alternatively, the waveforms 400 and 410 may be generated from data recorded by the pacer device 10 or the programmer 20 some time previously or during programming of the cardiac pacer 10. This may be achieved in different ways. For example, when the programmer 20 is started, the initial waveforms 400, 410 displayed in the uppermost windows 408 and 409 will a further screen of the graphical user interface. Here the same curve 400 is depicted as in FIG. 6. Two threshold levels 406, 407 are shown in the form of horizontal lines. The uppermost line 406 in FIG. 7 represents the atrial capture threshold and the lower line 407 represents the evoked response (ER) sensitivity threshold, which relates to ventricular stimulation. Fixed points 405 are located on the central horizontal axis of the curve 400. Movable points 404 are located on the lines 406, 407. These lines 406, 407 are thus movable with respect to the central (horizontal) axis of the curve, whereby an increase in the distance between a threshold line and the central axis causes an increase in threshold value, and a decrease in distance results in a decrease in threshold value. In the illustrated example, the evoked response sensitivity threshold value 407 can be viewed or set by moving the line. The atrial capture threshold preferably is used to indirectly adjust the atrial pulse width, and so adjust the atrial pulse energy. Reducing the threshold level by moving the line 406 towards the central axis of the curve 400 results in an increase in the atrial pulse width, while an increase in the threshold level 406 causes a reduction in atrial pulse width.

For the example of a cardiac pacer described with reference to FIGS. 2 and 3, it is possible to represent substantially all programmable parameters and illustrate all tests utilizing waveforms which are graphical representations of a ECG cycle showing pacer stimulation pulsed and a ECG waveform of spontaneous activity.

As mentioned above, the waveform used to represent programmable parameters of an implanted medical device 10 may be derived from data collected by the device 10 itself or even from the programmer 20. Thus, for example, a programmer 20 of an implantable cardiac pacer 10 may utilize ECG or IEGM curves to depict the parameters, which are routinely recorded by the pacer 10, and sometimes the programmer 20, during follow-up visits by the patient at a clinic or surgery. This brings with it the possibility of utilizing a waveform that is generated from the recorded data, to provide a real picture of the effects of programming parameters. This possibility is utilized in a further embodiment of be simulated waveforms that are stored in the programmer 20. As a follow-up procedure progresses and measured data is obtained from the cardiac device 10 or the programmer 20, the waveforms 400 and 410 are replaced by a waveform based on the measured data. For example, the stimulated ventricular pulse amplitude may be measured by the pacer output stage. This values combined with the IEGM measured by the pacer 10. can then be combined to form a waveform 400 for programming. Since the measured ECG or IEGM waveform will vary slightly from cycle to cycle, the displayed waveforms 400 and 410 may be generated using the averaged data for several measured ECG or IEGM cycles.

Figure 9:
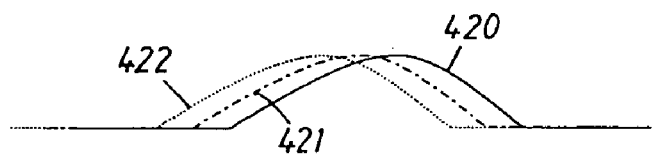
FIG. 9 illustrates a variation of the embodiment of FIG. 8.

In a further embodiment of the invention, the effects of varying the parameters as described with reference to FIGS. 7 and 8 is not shown using a continuously varying waveform as depicted in the lower window of FIG. 8. Rather the most recently available single waveform cycle is depicted with a number of earlier cycles shown offset from the most recent cycle. This is illustrated in FIG. 9. A current waveform 420 is depicted by a continuous line, earlier cycles 421 and 422 are depicted with dashed lines. In addition to being offset, earlier cycles are preferably also depicted in a contrasting shade or color is illustrated by the different broken lines in FIG. 9. This provides the operator with immediate feedback of the effects of altering one or more parameters.

In the exemplary embodiment using a programmer for a cardiac pacer, the parameters are linked to a representation of an ECG or IEGM signal. It will be appreciated that a measured or simulated ECG or IEGM waveform could equally be used to control intracardial devices (ICD) and devices for emerging indications (EI), for instance. In the case of devices for emerging indications (EI), which stimulate both sides of the heart, IEGM curves representing or measured from different sides of the heart can be compared and manipulated relative to one another to modify parameters that control the timing between the sides of the heart. It will be understood that the invention is not limited to ECG or IEGM waveforms. Any quantity that may be represented graphically and that is influences by or influences the operation of an implantable medical device can be used for programming the device. The choice of quantity depends on the workings of the device and the types of parameters to be programmed. For example programmers for drug pumps may utilize a representation of the heart rate or respiration rate, neurostimulators may utilize waveforms representing electrical activity in the brain.

The monitoring of a patient's condition and the pacer device activity through data collected and recorded by the implanted pacer device is generally accomplished during routine follow-up visits of the patient to a clinic. During these follow-ups, it is common for the operators of the programmer 20, who are typically medical practitioners, to follow predetermined sequences of steps to evaluate the patient's condition and the implanted device. These steps will often vary from operator to operator and also from clinic to clinic reflecting different personal preferences. However, it can also be useful to have different follow-up sequences for different pacer devices and possibly also different patient diagnoses. In accordance with a further embodiment of the invention, the programmer 20 suggests follow-up sequences to the operator that are based on the past behavior of the operator. Specifically, when an operator uses the same sequence of steps as during a previous follow-up, the programmer 20 suggests the creation of a follow-up script based on these repeated actions. Specifically, the programmer 20 displays a message requesting whether an automatic follow-up procedure should be generated. If the operator answers yes, the programmer 20 displays the sequence of steps followed previously. For example, the suggested steps may be 1) Check the atrial lead impedance, 2) Check ventricular lead impedance, 3) Perform atrial capture test, 4) perform ventricular capture test, 5) perform atrial sense test, 6) perform ventricular sense test, 7) read diagnostics. The operator is invited to confirm or reject each step and also to add functions not suggested by the programmer. Once the script has been completed, it is saved with a unique name. The operator also has the option to select criteria for when the script should be used, for example for a specific pacer model and patient diagnosis. Naturally, this requires the patient diagnosis to be recorded in the programmer along with a patient ID. Whenever a predefined follow-up script is selected by an operator, the programmer guides the operator automatically through the various steps by displaying the defined screens of the user interface. These follow-up scripts may also be linked to a particular operator identification code, so that each time the operator identifies himself to the programmer 20 with his identification code, the programmer 20 proposes his personalized follow-up procedures. Alternatively, the follow-up procedures may be available to all operators. This may help an operator, who is less experienced in the use of the programmer 20 to nevertheless perform rapid and complete follow-ups.

In accordance with a further embodiment of the invention, the operator is also able to generate follow-up scripts without prompting by the programmer 20. This is described with reference to a flow chart in FIG. 10. In the flow chart the follow-up procedure begins at step 300. The operator is invited to input his user ID, and preferably also his or her password, and the model and serial number of the cardiac pacer 10 is likewise identified by the programmer in step 301. This information is obtained from the pacer 10 directly through the telemetry link 26 either after interrogation by the programmer 20 or voluntarily by the pacer 10. Once the operator and device 10 are identified, the programmer 20 checks for scripts previously stored for the same operator and the same device type in step 302. If a script does exist, this script is run and the automatic follow-up procedure previously designed by the operator is performed in step 303. If several scripts exist for the same operator and device type, the operator is invited to select one procedure. After completion of this existing follow-up procedure, the operator is then given the opportunity to terminate the follow-up in step 304. If he or she replies yes, the follow-up procedure is ended in step 305. If the operator desires to continue the follow up at step 304 or alternatively, if no follow up script exists at step 302, the procedure moves on to step 306, where the operator performs some follow-up action using the programmer 20, for example setting a parameter value or performing a capture test. As the operator performs this action, the action is recorded by the programmer 20 in step 307. This process is repeated for all subsequent steps performed by the operator. When in step 308 no further action is performed, the programmer generates a follow-up script based on the recorded actions in step 309. In step 310, this script is compared with previously stored scripts. If a similar script exists, the programmer 20 decides in step 311 to end the follow-up and proceed to step 305. If no similar script exists, the programmer 20 presents the steps of the suggested script to the user on the display 24 in step 312. The operator is given the option to retain the script in step 313, in which case the script is stored in the storage unit 28 in step 314 and the follow-up terminated. If the operator rejects the script in step 313, the programmer 20 proposes the modification of the script in step 315. If the operator agrees to modify the script, this is done in step 316 after which the operator is again presented with a suggested script in step 312. If, on the other hand, the operator does not wish to modify the script in step 315, the follow-up terminates in step 305.

The user actions described in relation to the automatic generation of follow-up scripts relate not just to the selection of a particular parameter value, but to all actions performed using the object-oriented graphical user interface. For example, if the operator selects an object in the graphical representation, this is logged to a script file. Preferably the script file is a text file, although compressed files may be used if disk space is limited. The script file is preferably named automatically using the user id and device id, and possibly the patient diagnosis. If the sequence of actions performed by an operator were the following: selecting the right atrium, selecting atrial capture test, selecting right ventricle, selecting ventricular capture test, selecting an atrial sense test, selecting a ventricular sense test, closing the right atrium specification, closing the right ventricle specification, then a script file might have the following form:

OPEN_RIGHT_ATRIUM
A_CAPTURE_TEST
OPEN_R_VENTRICLE
V_CAPTURE_TEST
A_SENSE_TEST
V_SENSE_TEST
CLOSE_R_ATRIUM
CLOSE_R_VENTRICLE

When the operator desires to repeat this same follow-up procedure, the script is called up and the programmer reads the script file and simulates the actions of the operator. For example, in the first screen of the object-oriented user interface, the right atrium would first be highlighted indicating selection, and the right atrium object specification would then be displayed. The right-atrium capture test would then be performed, and so on.

Figure 11:
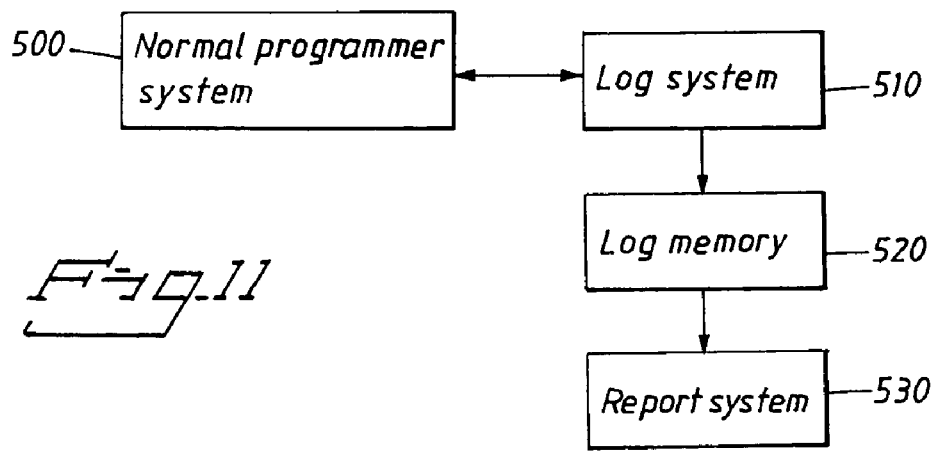
FIG. 11 schematically illustrates an overview of the programmer system for collecting statistical data in accordance with the invention.

In addition to memorizing user actions for use in follow-up procedures, the programmer according to the present invention is also adapted to record the utilization of all or only select functions of the programmer 20 to aid in the compilation of statistics. This is important for the evaluation of a particular programmer or a particular function of one or more programmers. This is described with reference to FIG. 11, which shows an overview of the programmer system. The overview in FIG. 11 includes the normal programmer system 500, which assures all the functions previously described as well as those functions not specifically described, but conventionally performed by a programmer. A log system 510 is provided which communicates with the programmer system 500 to obtain data relating to various events, such as the activation of one or more tests, the model of the pacer device 10 interrogated, parameter settings, and any other data related to the operation of the programmer 20. The collected information is stored in a non-volatile memory 520 connected to the log system 510. Preferably all information is stored together with the date and possibly also the time at which it was created. The model and serial number of the pacer device 10 interrogated also may be stored together with each piece of information. In this way, there is no risk of duplicating data. The date of creation of particular information may also be significant for subsequently compiled statistics. A report system 530 also accesses the log memory 520. This report system is connected to an external interface (not shown), for example, via serial line protocols or data networking protocols. Data contained in the log memory may then be downloaded via this external interface, possibly to a database. The extraction of data through this external interface may be accomplished in several ways. For example, the programmer 20 could be temporarily connected to a network or to a dial up connection and the data downloaded remotely. Data extraction may be performed on site, for example, by sales or service personnel using a direct serial cable. Alternatively, data may be stored in memory cards, for instance, a PCMCIA card, which is replaced at intervals, for example once a year.

Although modifications and changes may be suggested by those skilled in the art, it is the invention of the inventors to embody within the patent warranted heron all changes and modifications as reasonably and properly come within the scope of their contribution to the art.

We claim:

1. An arrangement for monitoring operation of an implantable medical device, comprising:
   a display for displaying respective movable representations of a plurality of objects;
   a user interface in communication with said display allowing a user to selectively move, on said display, said respective movable representations of a plurality of objects to form a graphical representation on said display of an area of interaction of a medical device within a patient, said graphical representation including at least one independently selectable object;
   an association unit for associating features for controlling said medical device, selected from the group consisting of parameters and functions, with said objects;
   said user interface including a selection unit for allowing a user to select at least said independently selectable object;
   said display being automatically responsive to selection of said at least one independently selectable object to display said feature associated therewith for review of said feature associated therewith on said display; and
   a communication unit connected to said display for establishing a communication linkage with said medical device, and being operable to selectively implement said feature associated with said at least one independently selectable object.

2. An arrangement as claimed in claim 1 comprising a programming unit interacting with said display, to allow modification of said feature, and interacting with said communication unit for programming said medical device in accordance with the modified feature.

3. An arrangement as claimed in claim 1 wherein said display displays at least one anatomical structure in a cardiovascular system of the patient associated with operation of said implantable medical device, as said graphical representation.

4. An arrangement as claimed in claim 1 wherein said display includes a representation of at least a part of said implantable medical device in said graphical representation.

5. An arrangement as claimed in claim 1 comprising an input unit for receiving an operator identification code, a comparator for comparing said operator identification code with stored identification information, and wherein said comparator allows said display to display said graphical representation only if said operator identification code corresponds with said stored identification information.

6. An arrangement as claimed in claim 5 wherein said display enables manipulation of said feature as a function of said stored identification information.

7. An arrangement as claimed in claim 6 wherein said display displays a predetermined, selectable object in said graphical representation as a function of said stored identification information.

8. An arrangement as claimed in claim 1 further comprising an input unit for receiving a medical device identification code, a comparator connected to said input unit for comparing said device identification code with stored identification information, and wherein said display is connected to said comparator and displays said graphical representation and enables manipulation of said feature as a function of said stored identification information.

9. An arrangement as claimed in claim 8 wherein said display displays a predetermined, selectable object in said graphical representation as a function of said stored identification information.

10. An arrangement as claimed in claim 1 wherein said display, in said graphical representation, displays a representation of at least one measurable physiological activity influenced by said medical device and wherein said feature is associated with dimensions of said representation of at least one measurable physiological activity, and said arrangement including a user-operable input unit for selecting and altering, in said graphical representation, a shape of the representation of at least one measurable physiological activity to display a desired operational effect of said medical device on said measurable physiological activity, and a modification unit connected to said display which is responsive to the altered shape of the measurable physiological activity in said graphical representation to cause said communication unit to communicate with said medical device to modify said feature.

11. An arrangement as claimed in claim 1 comprising a user-operable input unit allowing an operator to manipulate said feature in said graphical representation, and a recording unit for recording and storing manipulations of said feature via said input unit.

12. An arrangement as claimed in claim 11 further comprising a program generator for generating program sequences for automatically manipulating said feature dependent on manipulations stored in said recording unit.

13. An arrangement as claimed in claim 11 wherein said recording unit stores said manipulations as a function of time, and further comprising a readout unit allowing access to the manipulations stored in said recording unit.

14. An arrangement as claimed in claim 1 wherein said medical device is a cardiac stimulating device.

15. A method for monitoring operation of an implantable medical device, comprising:
   displaying respective movable representations of a plurality of objects;
   on said display, manually selectively moving said respective movable representations of a plurality of objects to combine said respective representations of a plurality of objects to form a graphical representation on said display of an area of interaction of a medical device within a patient, said graphical representation including at least one independently selectable object;
   electronically associating features for controlling said medical device, selected from the group consisting of parameters and functions, with said objects;
   manually selecting at least said independently selectable object;
   in response to selection of said at least one independently selectable object, automatically displaying said feature associated therewith for review of said feature associated therewith on said display; and
   establishing a communication linkage with said medical device, if necessary to implement, in said medical device said feature associated with said at least one independently selectable object.

16. A method as claimed in claim 15 comprising interacting with said display to allow modification of said feature, and programming said medical device in accordance with the modified feature.

17. A method as claimed in claim 15 wherein the step of displaying comprises displaying at least one anatomical structure in a cardiovascular system of the patient associated with operation of said implantable medical device, as said graphical representation.

18. A method as claimed in claim 15 wherein the step of displaying includes displaying a representation of at least a part of said implantable medical device in said graphical representation.

19. A method as claimed in claim 15 comprising receiving an operator identification code, comparing said operator identification code with stored identification information, and allowing display of said graphical representation only if said operator identification code corresponds with said stored identification information.

20. A method as claimed in claim 19 comprising enabling manipulation of said feature as a function of said stored identification information.

21. A method as claimed in claim 20 wherein the steps of displaying comprises displaying a predetermined, selectable object in said graphical representation as a function of said stored identification information.

22. A method as claimed in claim 15 further comprising for receiving a medical device identification code, comparing said device identification code with stored identification information, and enabling manipulation of said feature as a function of said stored identification information.

23. A method as claimed in claim 22 wherein the steps of displaying comprises displaying a predetermined, selectable object in said graphical representation as a function of said stored identification information.

24. A method as claimed in claim 15 wherein the step of displaying comprises displaying a representation of at least one measurable physiological activity influenced by said medical device and wherein said feature is associated with dimensions of said representation of at least one measurable physiological activity, and selecting and altering, in said graphical representation, a shape of the representation of at least one measurable physiological activity to display a desired operational effect of said medical device on said measurable physiological activity, and in response to the altered shape of the measurable physiological activity in said graphical representation causing said communication unit to communicate with said medical device to modify said feature.

25. A method as claimed in claim 15 comprising allowing an operator to manipulate said feature in said graphical representation, and storing manipulations of said feature.

26. A method as claimed in claim 25 further comprising generating program sequences for automatically manipulating said feature dependent on stored manipulations.

27. A method as claimed in claim 25 comprising storing said manipulations as a function of time, and further comprising allowing access to the stored manipulations.

28. A computer program product including computer code embodied on a computer readable medium, for displaying a plurality of movable objects selected from the group consisting of representations of an implantable medical device and representations of an area of a patient interacting with a medical device, enabling a selective rearrangement of at least some of said objects to form a manual graphical representation of an area of interaction of said medical device with a patient, defining at least one element of the graphical representation as an independently selectable object, associating parameters for controlling operation of said medical device with portions of said graphical representation such that manual selection of one of said objects causes automatic display of a feature associated therewith, selected from the group consisting of parameters and functions.

* * * * *